United States Patent [19]
Gabbai

[11] Patent Number: 5,632,955
[45] Date of Patent: May 27, 1997

[54] MICROWAVE STERILIZER FOR METAL OBJECTS

[75] Inventor: Eran Gabbai, Petach Tikuch, Israel

[73] Assignee: Vibrenergy Ltd., Jerusalem, Israel

[21] Appl. No.: 498,615

[22] Filed: Jul. 6, 1995

[51] Int. Cl.$^6$ ................................................ A61L 2/12
[52] U.S. Cl. ........................................ 422/21; 219/747
[58] Field of Search ................. 422/21; 219/745, 219/747

[56] References Cited

U.S. PATENT DOCUMENTS

| | | | |
|---|---|---|---|
| 3,946,187 | 3/1976 | MacMaster et al. | 219/747 |
| 4,621,179 | 11/1986 | Kusunoki et al. | 219/747 |
| 5,552,112 | 9/1996 | Schiffmann et al. | 422/21 |

*Primary Examiner*—Timothy McMahon
*Attorney, Agent, or Firm*—Gottlieb, Rackman & Reisman, P.C.

[57] ABSTRACT

An apparatus uses microwave radiation to sterilize metal equipment including sharp edged metal equipment having small quantities of water or water containing organisms on the surface of the equipment. No source of bulk water is required to be heated during the sterilization process and no humid environment is required. The microwave radiation is emitted from locations at opposing ends of a wave guide so that the equipment is present at a nodal point of the near electric field component of the microwave radiation. This configuration reduces the electromagnetic field components that induce sparking and avoids the formation of large potential differences induced by the microwave field between the equipment and the microwave cavity walls. In addition the apparatus employs the electron cloud located in the near field of the magnetron to bombard the surface of the equipment.

The microwave radiation is generated by a magnetron unit providing about 300 watts without of power without any significant potential difference between the equipment to be sterilized and the magnetron.

2 Claims, 2 Drawing Sheets

MICROWAVE STERILIZER FOR METAL OBJECTS

This invention relates to apparatus employing microwave fields for the sterilization of metal instruments including those having sharp edges such as dental tools. It further relates to such apparatus having wave guides for microwave fields that do not induce sparking at sharp metallic surfaces.

BACKGROUND OF THE INVENTION

The sterilization of metal instruments is typically accomplished by apparatus that heats the instrument to a temperature at which the biological infecting organism is killed. This process is both costly and slow and many attempts have been made to develop processes that directly attack the organism without the overhead cost of heating the instrument. Processes, such as are disclosed in U.S. Pat. No. 5,039,495 have utilized chemical agents to attack the organisms or as disclosed in U.S. Pat. No. 5,325,020 have used physical agents such as gaseous plasmas. In connection with those processes microwaves have been used to heat the chemical agent or to induce the plasma. Other systems such as that disclosed in U.S. Pat. No. 4,861,956 have utilized aqueous environments in which water is heated to a gaseous phase which contacts and destroys the organism. In each of the systems where metal instruments are sought to be sterilized in the presence of microwave radiation the tendency of arcing to occur in the presence of sharp edges of the instruments has been a limitation of the process.

Microwave systems have been used for selectively heating the water contained in organic material. Microwaves are electromagnetic radiation having a frequency that is associated with a wavelength in the centimeter range. A preferred value is 6.25 cm. The relation between frequency and wavelength is essentially trivial: frequency=(speed of light)/wavelength.

Microwave frequencies may conveniently be chosen having frequencies that are resonantly absorbed by water molecules but not by the molecules of most plastic and ceramic materials. Thus intense microwave energy focused on an organic material may be selectively absorbed by the water contained in the material. Two benefits of microwaves are that a ceramic container for the material is not heated by the microwaves and the object is heated uniformly throughout, wherever water molecules are present. Thus one does not have to wait while heat diffuses from a heated container to the outer surface of the material to be heated and then diffuses inwardly. This has attracted many attempts to utilize microwave energy for the selective destruction of water bearing microorganisms on metal surfaces.

Metal surfaces in the presence of intense microwave radiation have a number of properties that detract from the usefulness of microwaves to sterilize such surfaces. A metal surface supports electric currents that generate intense electric and magnetic fields close to the surface. The intensity of such fields is dependent upon the radius of curvature of the metal surface, being more intense in the vicinity of a sharply curved surface and most intense in the vicinity of a discontinuity of the curvature of the surface such as would be found near a sharp metallic edge. These strong electric fields cause the local ionization of any humidity present close to the surface. The ionized humidity then supports the formation of electrical arcs resulting in an alternative path for the release of the energy from the source of microwave energy to the metal surface. Instead of the desired heating mode, the high power output of the microwave generator produces a high current density in the spark that follows the ionization path and will burn the instrument. Furthermore, once the arc is created it tends to become self sustaining and draws large currents for a relatively long period of time, sufficient to destroy the sharpness of the instrument being sterilized.

A second property of highly conductive materials is that they act as a mirror for the source of microwave radiation. Thus in the presence of a metal surface there appear virtual microwave sources as intense as the original source. These virtual sources have required the prior art to adopt shielding so as to prevent the destruction of the actual source of microwave radiation.

U.S. Pat. No. 4,861,956 assigned to Magnetronics, Inc. is for a "Microwave/Steam Sterilizer." This apparatus is a sterilizer that forms an atmosphere of gaseous water and electromagnetic energy. It is designed to operate at relatively low temperatures and for short periods of time. It tries to deal with the difficulty of using microwave energy to kill dry spores by having a water reservoir, and the tendency of microwave apparatus to self-destruct from its own energy. It comprises a waveguide conduit having a terminal aperture located one quarter wavelength from the bottom of a water reservoir and subapertures spaced one quarter wavelength from each other. The waveguide and walls of its working cavity are angled to avoid the reflection of microwave energy back to the microwave energy generator. The patent speaks of a synergy of steam and microwave energy. To accomplish this, a pool of water acts as a receptor for microwaves, and in turn provides a source of required steam and a trap to prevent the microwave energy from destroying the microwave source. The patent is concerned about the microwave energy that is reflected back to the microwave source from electrically conductive surfaces. The water is designed to act as a trap to minimize the entrance of reflected energy. A distance from the microwave outlet of one quarter wavelength from the water surface is optimal for that trapping effect.

U.S. Pat. No. 4,952,763 assigned to Snowdrift Corp. of the Netherlands Antilles is for a "System For Heating Objects With Microwaves". Two microwave frequencies are used to heat a sealed package at temperatures above 80° C. placed at the geometric location where the sum field occurs. Two magnetron emitters are employed having about the same frequencies and amplitudes and radiate from opposite sides of a work space at a low frequency alternating cycle. The interference pattern from the emitters furnishes high energy concentration in parts or over all of the object to be heated. An alternative to two separate emitters is to employ a single emitter formed from one annular hollow waveguide with symmetrically disposed coupling in and coupling out locations. A pressure-tight working area can be formed by part of this hollow conductor at the coupling out location. A quarter wavelength displacement of the two coupling in points is said to generate homogeneous heating.

U.S. Pat. No. 5,039,495 assigned to Flexiclave, Inc. is for an "Apparatus For Sterilizing Articles Such As Dental Handpieces". This patent discusses prior art patent 4,400,357 which uses a liquid reaction agent and microwave radiation restricted to a narrow liquid-containing vessel while the article to be sterilized is kept outside the radiation field, in order in order to avoid the formation of spark gaps at border surfaces and seams of the article which causes surface destruction. This patent also discussed prior art patent 3,753,651, which concerns the non-thermal effects of microwave radiation and notes the improvement in sterilization that occurs in a humid environment when microwave radiation is present. The disclosure of U.S. Pat. No. 5,039, 495 is itself concerned with a microwave transparent pouch into which the instruments and a sterilant solution is placed within the cavity of a microwave radiator. The patent says that surprisingly no arcing occurs despite microwave irradiation of the metal instrument. The patent suggests an alternative embodiment in which a shield is used to prevent the microwaves from reaching the metal instruments. Apparently, (Col. 9 line 8), this patent discloses that it would not be possible to simultaneously sterilize several instruments, or one with sharp edges, without having arcing occur. Therefore, the patent teaches that the instruments should be surrounded with a shield that bars the transmission of microwave radiation, such as a double layered knitted mesh of tin-copper-steel wire. It should be noted that all the claims of this patent require shielding of the instruments from the microwave radiation.

U.S. Pat. No. 3,753,651 issued to Wave Energy Systems Inc. for a "Method And Apparatus For Surface Sterilization". This uses a microwave energy field combined with a humid atmosphere of at least 50%. The inventors state that the prior art failed to find a commercially suitable use of microwaves for sterilization because it did not maintain the correct humidity level of the irradiated microorganisms. The material to be sterilized is placed into a container that is transparent to the microwaves while a moist atmosphere is confined to the interior of the container. The patent mentions the non-thermal effects of microwaves such as chemical bond breaking, accelerated diffusion of ions through membranes, and PH modification and mentions the surface-sterilization of dental tools at lower temperature than dry heat and steam sterilizers. The apparatus appears to be a conventional microwave oven with an internal structure designed to maintain the humid environment in contact with the devices to be sterilized.

U.S. Pat. No. 5,325,020 issued to AbTox, Inc. for a "Circular Waveguide Plasma Microwave Sterilizer Apparatus". This employs a microwave plasma generator for producing a gas plasma generated from a gas mixture of oxidizing and/or reducing agents. The microwaves enter a sealed gas containing chamber which is transparent to the microwave energy. It is the contact of microorganisms with the plasma that results in their destruction.

The foregoing patents require for the most part an artificial environment providing a combination of an aqueous environment with a source of microwave radiation the heat water in the environment. Those that use destructive interference of microwaves do so to avoid the effects of the reflection of microwaves from the surfaces of bulk water that is provided to form a pool to supply a relatively high humidity value in the vicinity of the apparatus to be sterilized. None of the prior art attempts to control the location of the intense radiation in the vicinity of the object to be sterilized other than by the use of electromagnet shields. None of the prior art is concerned with minimizing the electric field in the near field zone of the microwave source. Furthermore, none of the prior art attempts to utilize the thick cloud of electrons located in the near field of the magnetron to sterilize organisms residing on materials including sharp edged conductive metal surfaces.

BRIEF DESCRIPTION OF THE INVENTION

The present invention is an apparatus designed to sterilize metal equipment including sharp edged metal equipment having small quantities of water or water containing organisms on the surface of the equipment. The invention avoids the formation of large potential differences induced by the microwave field between the equipment and the microwave cavity walls. In particular the invention creates a near field region in the vicinity of locations at opposing ends of a wave guide or antennae placed at a distance in the order of a wavelength apart. The equipment to be sterilized is present in this near field region preferably near a nodal point of the electric field component of the microwave radiation. Thus, the sterilization region is characterized by the absence of strong electric fields and the presence of strong magnetic fields. This configuration reduces the electromagnetic field components that induce sparking; there may remain a strong magnetic flux which kills organisms, resulting in sterilization. In addition, the apparatus may employ an electron cloud derived from that located in the near field of the magnetron to bombard the surface of the equipment. Thus, the apparatus relies at least in part on microwave effects other than the radiation energy absorption by water to effect sterilization. By near field of a source is meant a region extending from the source a distance which is on the order of magnitude of the radiation emitted from the source.

The microwave radiation is generated by a magnetron unit providing about 300 watts of power. This occurs without any significant potential difference between the equipment to be sterilized and the magnetron. The invention is believed to be the first use of a pair of waveguides to bring microwave radiation from a magnetron into destructive interference of the electric field component of the microwave field near a surface to be sterilized or to use the electron cloud in the magnetron near field to effect sterilization.

The magnetron radiation is believed to induce in the micro organisms to be destroyed secondary effects upon the electrons in the organisms so that in addition to any thermal effect of the microwave field absorbed by moisture there are additional effects due to the magnetic order of the microwave radiation that destroy the micro organism. Such effects may include pH alteration or chemical bond breaking and may include direct electron bombardment.

It is an object of the present invention to provide an arrangement of paired waveguide outputs that provide a large near field region in which the electric mode of electromagnetic radiation which would cause sparking or overheating of metal objects is suppressed.

It is a further object of the present invention to provide an electric nodal near field region in the vicinity of the objects to be sterilized resulting from the positioning of the output of waveguides or antennae from a single radiation source having a relative displacement that is related to the wavelength of the microwave radiation.

It is a still further object of the present invention to provide apparatus for enhancing the bombardment of metal surfaces by electrons from the cloud that forms in the near field of a magnetron microwave source.

DETAILED DESCRIPTION OF A PREFERRED EMBODIMENT

Figure 1:
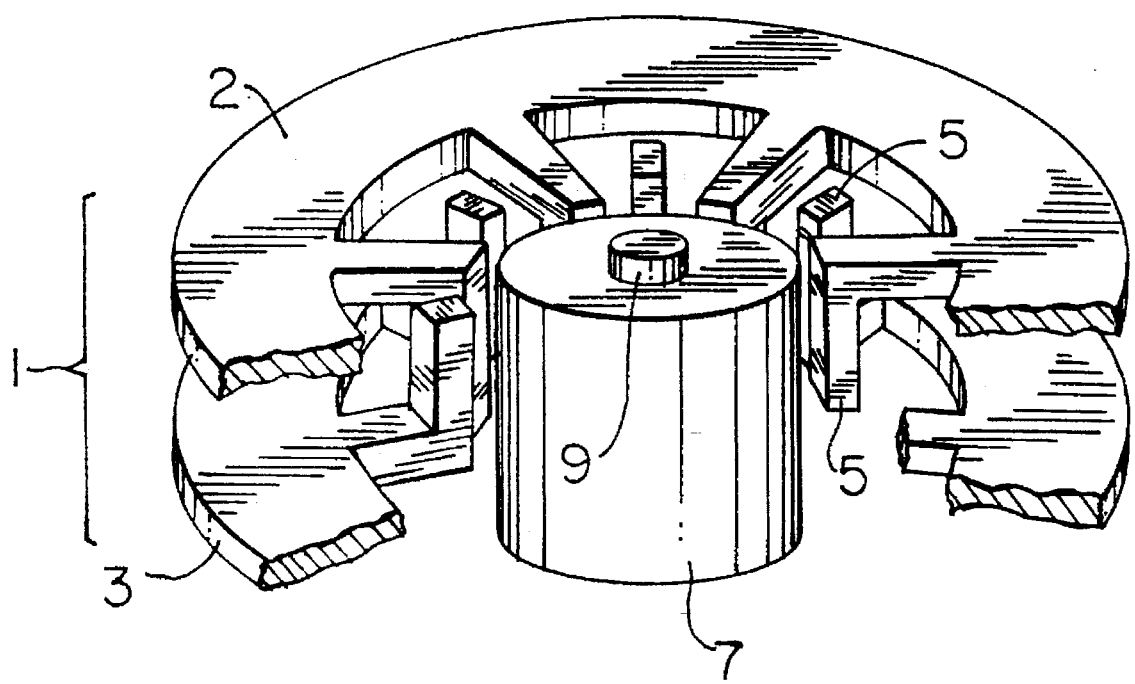
FIG. 1 is a cross sectional view of a magnetron tube which is the source of microwave radiation for the present invention.

FIG. 1 shows a cut away view of the interior of a magnetron tube which supplies microwave radiation for the present invention. The tube contains an axially symmetric anode ring 1 comprised of upper 2 and lower 3 axially symmetric segments. These segments have upward and downward depending resonators 5 which form the anode into a resonant chamber having dimensions equal to one quarter of the wavelength of the radiation to be emitted. Centrally and axially symmetrically located is a cathode 7 that surrounds a heater element 9. A strong magnetic field is imposed along the axis of the magnetron tube and a high potential difference is imposed between the anode 1 and the cathode 7. The resulting electromagnetic fields result in large electron emission from the heated cathode across to the anode which is accompanied by the radiation of microwave radiation typically at a power lever of several hundred to a few thousand watts and frequencies between 3,000 and 3NO" Hz.

The present invention utilizes both the intense microwave radiation and the attendant electron cloud formed in the magnetron for the sterilization of biologic organisms on the surface of sharp edged metal instruments such as dental tools. It has been surprisingly discovered that if the microwave radiation is supplied from the ends of a wave guide symmetrically placed about the object to be sterilized and having dimensions such that the radiation emerging at each end is shifted in phase by 180°, the sterilization takes place without significant heating of the object's surface and without sparking between the object and the magnetron. It is believe that two phenomena account for this effect. One is the presence of a node of the electrical component of the magnetron field in the vicinity of the object which results in the suppression of arcing from the sharp edges of the objects to be sterilized. This is a very surprising result since the prior art would lead one to expect that the sterilization of metallic surfaces by microwaves could only be accomplished either by the complete shielding of the objects from the intense microwave field and relying entirely upon thermal effects, or by the requirement of an environment of high humidity so that some secondary effect involving the presence of water in the environment suppressed the arcing that would be expected. The other phenomena is the presence of electrons from the magnetron emerging from the ends of the wave guide and bombarding the object and its biological contaminant. The presence of electrons of sufficient energy at the end of the wave guides is a second unexpected effect of the present arrangement. These electrons may have their origin in the strong cathode current within the magnetron or may be a secondary source derived from the ionization of material found between the magnetron and object to be sterilized. The electron bombardment results in the death of the organisms residing on the objects surface without dependence upon any thermal heating effect. These effects may be accompanied by direct microwave absorption with its attendant thermal heating effects upon the organisms. The presence of these effects in the vicinity of a node of the electrical component of the microwave field is believed to be due to the presence of strong magnetic components in the near field of the terminal ends of the waveguide, in particular, modes of the electromagnetic field associated with the microwave radiation.

Figure 2:
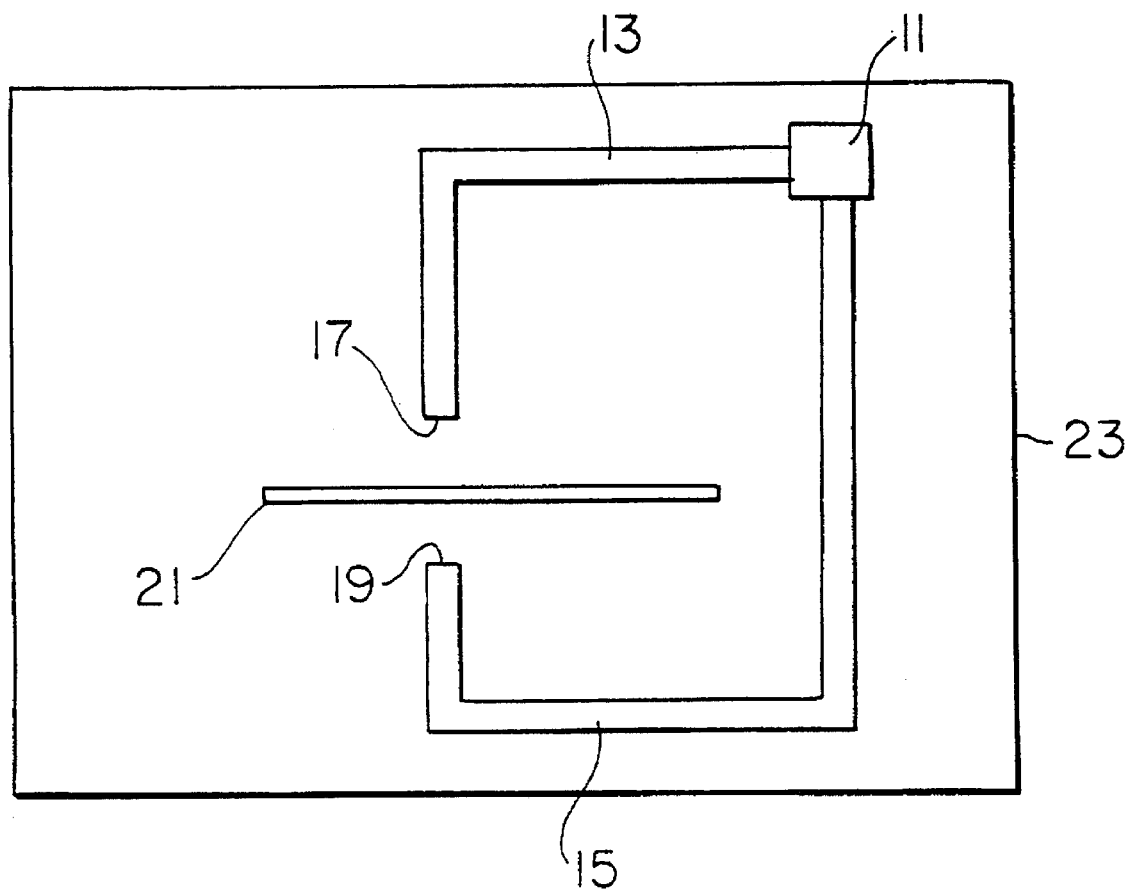
FIG. 2 is a schematic drawing of the microwave radiation sterilization apparatus of the present invention.

FIG. 2 depicts the microwave sterilization device of the present invention. The magnetron 11 is provided with at least one pair of metallic wave guide arms 13, 15, which may be of rectangular cross section. The dimensions of the wave guide cross section determines the radiation that they may pass as is well known in the art. See for example, Jackson, "Classical Electrodynamics", 1962, chapter 8. In particular the largest linear dimension should be at least as great as the wavelength of the microwave radiation to be transmitted through the wave guide. The length of the arms of the wave guide are adjusted so that the electric field emitted from the ends 17, 19 of the wave guides has a node at the midpoint of the line joining the ends. This may be accomplished by making one arm of a symmetrical arrangement of wave guides longer than the other arm by a length equal to one half the microwave wavelength output from the magnetron.

A platform 21, preferably of some plastic or ceramic material transparent to microwaves in order to avoid extraneous heating is positioned midway between the ends of the wave guides. There is no criticality to the precise location of the platform within the near field of the radiation since the misalignment will merely result in some small thermal heating, which would further contribute to the sterilization of the organisms. The entire apparatus is enclosed in a metal container 23. The walls of the container may be coated with energy-absorbing material to prevent the build-up of energy beyond the near field. Such materials may be carbon-based.

The container 23 is not essential to the invention because it is neither necessary to contain the build up of heat nor are there strong microwave fields that require shielding from the environment. The container is present to enhance the effect of the radiation by providing a reflection surface for the emitted waves and to function as a safety precaution in the event of malfunction of the apparatus. The container may also be a Faraday cage with one or more openings into which a magnetron transmits energy through two or more antennas passing through the walls of the cage. It is required that the antennas shift the wave length of the entering radiation so that opposing phases are present in the neighborhood of the platform. The phase relation may be influenced by varying the circumference or material composition of the antennae. The radiation from the magnetron may be either steady or pulsating so long as the wavelength of the radiation is appropriate to maintain the desired phase relationship.

In addition to a description of what the apparatus of the present invention contains it is significant what has been omitted from the apparatus of the prior art. In particular no source of bulk water is required to maintain a humid environment for the operation of the present invention. There is also no need to contain the object in any form of envelope in order to contain heat or to protect the object from arcing of an electronic current to the metal container or to the microwave source. The apparatus operates without significant heating of the surface to be sterilized and thus no thermal insulation of the device is required. Thus the present invention is a significantly simpler and less costly device for accomplishing the destruction of biologic organisms on the surface of sharp edged conductive objects. It should be noted that where the direct bombardment by electrons occurs, it is not necessary that the organisms that are destroyed contain significant quantities of water. Thus the device is effective against spores as well as other organisms. Because of its low temperature operation, the invention has particular applications not heretofore associated with microwave sterilization. Examples are sterilization of fresh vegetables, sterilization of air passing through the near field (which may be incorporated into an air conditioning unit).

Where sharp edged metal objects are not going to be sterilized, the maintenance of a nodal near field region is not as critical. In this way, for example, a microwave clothes dryer that tolerate some metal objects, such as zippers are now possible.

Although the invention has been described in terms of a preferred embodiment it is intended that the scope of the protection for the invention afforded by this patent not be limited to the specific preferred embodiment, but be governed by the proper interpretation of the following claims.

I claim:

1. A method for sterilization of metal instruments comprising placing said instruments within a microwave field comprising separate microwave fields 180° out of phase at least one location on said instrument, said separate fields emerging from wave guide means within a container free from the presence of bulk water.

2. A method for sterilization of metal instruments comprising placing said instruments within a microwave field emerging from a microwave source and comprising separate microwave fields 180° out of phase at least one location on said instrument and bombarding said instruments with electrons emerging from the ends of waveguides extending from the microwave source, said separate fields emerging from wave guide means within a container free from the presence of bulk water.

* * * * *